United States Patent [19]

Alexander et al.

[11] Patent Number: 4,952,748

[45] Date of Patent: Aug. 28, 1990

[54] PURIFICATION OF HYDROCARBONACEOUS FRACTIONS

[75] Inventors: Richard A. Alexander; Charles E. Knight, both of Mobile, Ala.

[73] Assignee: Mobil Oil Corp., New York, N.Y.

[21] Appl. No.: 405,119

[22] Filed: Sep. 7, 1989

Related U.S. Application Data

[63] Continuation of Ser. No. 358,758, May 26, 1989, abandoned.

[51] Int. Cl.[5] .......................... C07C 7/10; C07C 7/12

[52] U.S. Cl. .......................... 585/803; 208/334; 208/335; 208/337; 208/341; 585/352; 585/825; 585/826; 585/867

[58] Field of Search .............. 585/867, 803, 823, 825, 585/826, 352, 350; 208/337, 334, 335, 341, 361, 311

[56] References Cited

U.S. PATENT DOCUMENTS

| | | | |
|---|---|---|---|
| 2,666,500 | 1/1954 | Cahn et al. | 585/823 |
| 3,094,569 | 6/1963 | Thomas | 585/823 |
| 3,567,791 | 3/1971 | Fuller | 585/857 |
| 4,083,772 | 4/1978 | Asselin et al. | 585/857 |
| 4,793,545 | 1/1989 | Schmidt | 585/823 |

OTHER PUBLICATIONS

"Operating Problems in the Hanlan Swan Hills Gas Field", by W. J. King, presented at the SPE Gas Technology Symposium Jun. 13-16, 1988, Dallas, Tex.

*Primary Examiner*—Asok Pal

*Attorney, Agent, or Firm*—Alexander J. McKillop; Charles J. Speciale; Robert B. Furr, Jr.

[57] ABSTRACT

A process is disclosed for extracting diamondoid compounds from a hydrocarbon gas stream. The process includes two stages, each of which alone is effective to remove diamondoids from a hydrocarbon gas stream. The first stage comprises contacting the diamondoid-laden hydrocarbon gas with a suitable solvent to preferentially dissolve the diamondoids into the solvent. Diesel fuel is the preferred solvent for this first stage. The second stage comprises sorbing diamondoids from the diamonoid-laden hydrocarbon gas with silica gel. The most preferred embodiment of the invention is a serial process in which a diamondoid-laden gas is first treated in the solvation stage and the partially purified gas is further resolved in the silica gel sorption stage. The invention still further includes a process for segregating adamantane and diamantane when both are separated from a hydrocarbon gas stream.

23 Claims, 1 Drawing Sheet

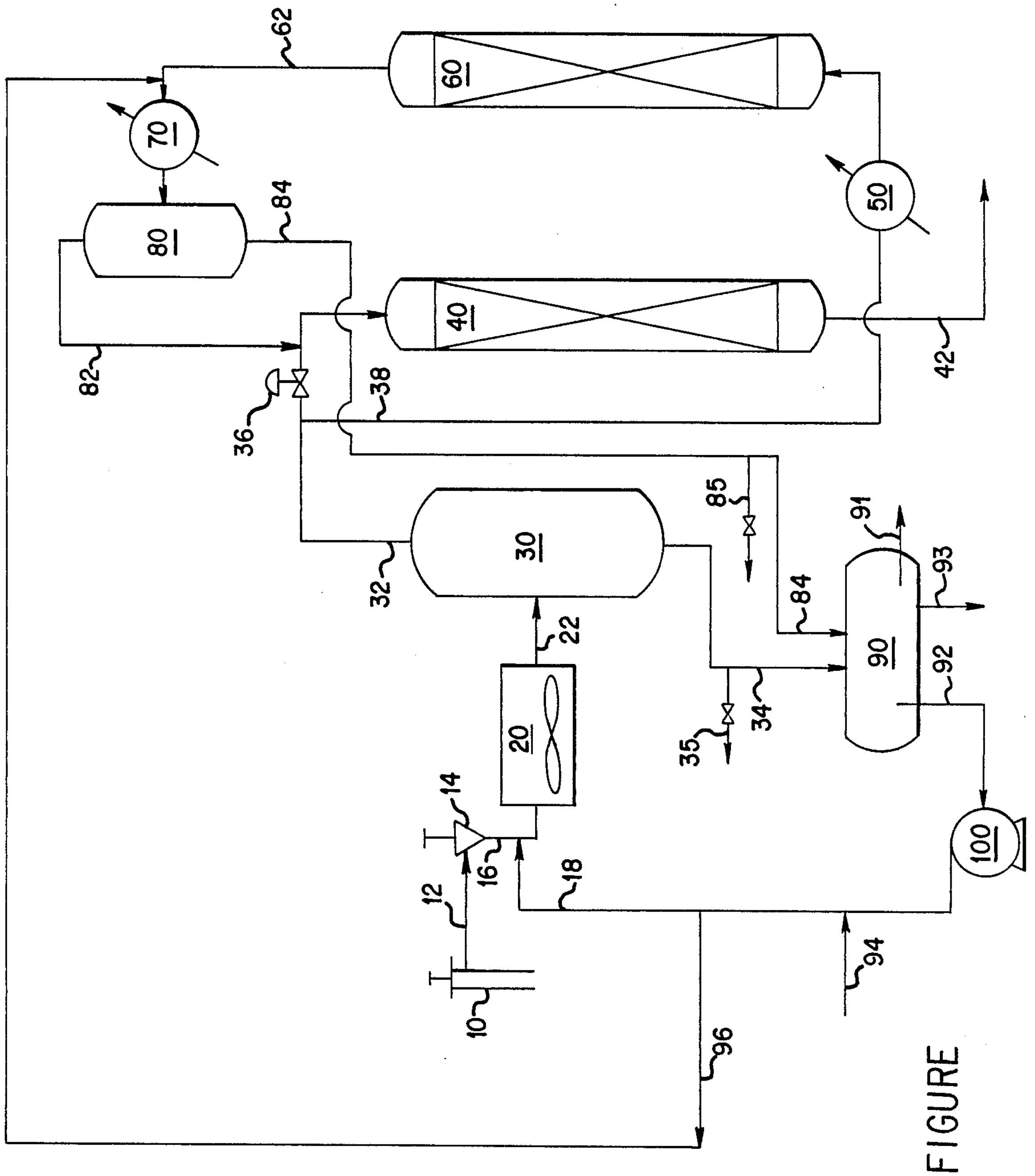
FIGURE

PURIFICATION OF HYDROCARBONACEOUS FRACTIONS

This is a continuation of copending application Ser. No. 358,758, filed on May 26, 1989, now abandoned.

BACKGROUND OF THE INVENTION

This invention relates to the removal of certain components from hydrocarbon streams. It more particularly refers to separating diamondoid organic compounds from hydrocarbon streams containing such.

Many hydrocarbonaceous mineral streams contain some small proportion of diamondoid compounds. These high boiling, saturated, three-dimensional polycyclic organics are illustrated by adamantane, diamantane, triamantane and various side chain substituted homologues, particularly the methyl derivatives. These compounds have high melting points and high vapor pressures for their molecular weights and have recently been found to cause problems during production and refining of hydrocarbonaceous minerals, particularly natural gas, by condensing out and solidifying, thereby clogging pipes and other pieces of equipment. For a survey of the chemistry of diamondoid compounds, see Fort, Jr., Raymond C., *The Chemistry of Diamond Molecules*, Marcel Dekker, 1976.

In recent times, new sources of hydrocarbon minerals have been brought into production which, for some unknown reason, have substantially larger concentrations of diamondoid compounds. Whereas in the past, the amount of diamondoid compounds has been too small to cause operational problems such as production cooler plugging, now these compounds represent both a larger problem and a larger opportunity. The presense of diamondoid compounds in natural gas has been found to cause plugging in the process equipment requiring costly maintenance downtime to remove. On the other hand, these very compounds which can deleteriously affect the profitability of natural gas production are themselves valuable products.

SUMMARY OF THE INVENTION

According to this invention, it has now been found that diamondoid compounds may be extracted from hydrocarbonaceous gas streams by contacting the gas stream with a liquid solvent in which diamondoid compounds are at least partially soluble. It has been found that the diamondoid compounds are preferentially dissolved from the gas stream into the selected liquid solvent thereby providing a method not only for preventing or reducing plugging of downstream process equipment but also for recovering valuable diamondoid compounds. Solvents useful in the solvation process of the invention include normally liquid hydrocarbons containing aromatics including petroleum-based solvents such as kerosene, diesel fuel, and heavy gasoline, with diesel fuel being the most preferred solvent.

Further, it has been found that a second separation step, silica gel sorption, is effective to sorb diamondoid compounds from a hydrocarbon gas stream. Depending upon the composition of the hydrocarbon gas stream, solvent addition may optionally be employed to reduce diamondoid deposition in the silica gel sorption equipment, with solvent injection to the silica gel regeneration circuit as described below being particularly beneficial.

Both diamondoid separation steps are employed in the preferred embodiment of the invention. The diamondoid compound-containing hydrocarbon gas stream is first contacted with a suitable solvent as described above. The gas/liquid mixture is then separated, e.g. flashed, to form an at least partially purified gas stream and a liquid solvent stream enriched in diamondoid compounds. If the diamondoid compound-containing gas stream to be purified is rich in substituted higher boiling point adamantane homologues, the solvation and gas/liquid separation steps may produce a gas stream having acceptable purity. If, however, if the diamondoid compound-containing gas feedstream contains a substantial fraction of less substituted lower boiling point adamantane homologues, the silica gel sorption step may be necessary to achieve the desired gas product stream purity or extent of diamondoid recovery.

The present invention, then, provides a solvation process for extracting diamondoid compounds from a gas stream comprising the steps of providing a gas stream containing a recoverable concentration of diamondoid compounds, mixing the gas stream containing diamondoid compounds with a solvent in which diamondoid compounds are at least partially soluble, controlling the conditions including temperature and pressure of the mixture to maintain at least a portion of the mixture in the liquid phase, separating the mixture under these controlled conditions into a vapor stream and a diamondoid-enriched solvent stream, and recovering diamondoid compounds from the diamondoid-enriched solvent stream. The process may further comprise recycling the diamondoid-enriched solvent stream to at least partially saturate the diamondoid-enriched solvent stream as well as adding fresh solvent and withdrawing solvent which is at least partially saturated with diamondoid compounds.

The invention further provides a sorption process for extracting diamondoid compounds from a diamondoid-containing gas stream comprising the steps of providing a gas stream containing a recoverable concentration of diamondoid compounds, contacting the diamondoid-containing gas stream with silica gel in a sorption zone under conditions of temperature and pressure to prevent substantial formation of solid diamondoid deposits in the sorption zone for a period of time sufficient for the silica gel to sorb at least a portion of the diamondoid compounds from the hydrocarbon gas, and regenerating the silica gel by contacting the silica gel with a regeneration fluid in which diamondoid compounds are at least partially soluble to desorb diamondoid compounds from the silica gel.

The preferred embodiment of the invention includes both the solvation and sorption stages, providing a process for extracting diamondoid compounds from a diamondoid-containing gas stream comprising the steps of providing a gas stream containing a recoverable concentration of diamondoid compounds, mixing the gas stream containing diamondoid compounds with a solvent in which diamondoid compounds are at least partially soluble, controlling the conditions including temperature and pressure of the mixture to maintain at least a portion of the mixture in the liquid phase, separating the mixture under the controlled conditions into a partially purified gas stream and a diamondoid-enriched solvent stream, recovering diamondoid compounds from the diamondoid-enriched solvent stream, contacting the partially purified gas stream with silica gel in a first sorption zone under conditions of temperature and pressure to prevent substantial formation of solid diamondoid deposits in the sorption zone for a period of time sufficient for the silica gel to sorb at least a portion of the diamondoid compounds from the hydrocarbon gas, and recovering diamondoid compounds from silica gel by desorption in a second sorption zone by contacting the silica gel with a regeneration fluid in which diamondoid compounds are at least partially soluble to desorb diamondoid compounds from the silica gel.

The preferred embodiment of the invention provides the completely unexpected ancillary benefit of segregating adamantane from diamantane when both are separated from hydrocarbon gas stream. The diamondoid-enriched solvent withdrawn from the first or solvation stage is rich in diamantane while the regeneration fluid used to desorb the silica gel in the downstream sorption stage is rich in adamantane. Consequently, the invention still further includes a process for fractionating adamantane from diamantane comprising the steps of providing a gas stream containing a recoverable concentration of adamantane and diamantane, mixing the gas stream containing adamantane and diamantane with a solvent which solvates diamantane preferentially to adamantane, controlling the conditions including temperature and pressure of the mixture to maintain at least a portion of the mixture in the liquid phase, separating the mixture under the controlled conditions into a adamantane-enriched gas stream and a diamantane-enriched solvent stream, recovering diamantane from the diamantane-enriched solvent stream, contacting the adamantane-enriched gas stream with silica gel in a first sorption zone under conditions of temperature and pressure to prevent substantial formation of solid diamondoid deposits in the sorption zone for a period of time sufficient for the silica gel to sorb at least a portion of adamantane from the adamantane-enriched gas, and recovering adamantane from silica gel in a second sorption zone by contacting the silica gel with a regeneration fluid in which adamantane is at least partially soluble to desorb adamantane from the silica gel.

DESCRIPTION OF THE DRAWING

The Figure is a simplified schematic showing major processing steps of a preferred embodiment of the present invention.

DETAILED DESCRIPTION

Referring now to the Figure, a preferred embodiment of the present invention is schematically illustrated. A diamondoid-laden natural gas stream 12 is withdrawn from wellhead 10 at high pressure, typically around 11,000 psig. Pressure reduction valve 14, commonly referred to as a choke, reduces the natural gas pressure downstream of the choke to between about 900 and about 1400 psig. Recycled solvent 18 is injected into the reduced pressure diamondoid-laden natural gas stream 16 upstream of process cooler 20 to prevent deposition of diamondoid solids within the cooler. Process cooler 20 is typically an air cooled exchanger with extended heat exchange tube surface area, commonly known as a fin-fan exchanger.

Solvent injection rates of about 2 to 6 gallons per minute (GPM) at natural gas flowrates of 10 to 15 million standard cubic feet per day (MMSCF/D) have been found to be effective to reduce diamondoid deposition. Thus to achieve the desired diamondoid sorption in the added solvent, solvent charge rates of about 100 to 1000 gallons per million standard cubic feet of natural gas (G/MMSCF) are acceptable, and rates of between about 200 and 800 G/MMSCF are preferred. The optimum charge rate within the disclosed ranges to minimize solvent costs while preventing diamondoid deposition in the downstream process equipment may be determined by one of ordinary skill in the art with a reasonable amount of trial and error.

If the solvent dosage selected for process operation is insufficient to maintain the diamondoids in solution through the process cooler, or if solvent injection is temporarily discontinued for operational reasons such as injection pump failure, diamondoids will likely be deposited on the inner surfaces of the process cooler heat exchange tubes, increasing the pressure drop across the air cooled exchanger. Thus one recommended method for determining optimum solvent dosage would be to monitor the change in natural gas pressure ($\Delta P$) across the process cooler with respect to time. An decrease in the $\Delta P$ across the process cooler would likely indicate diamondoid deposition on the inner surfaces of the cooler tubes and could be corrected with increased solvent dosage. The technique of monitoring heat exchanger operation by evaluating $\Delta P$ over time is well known to those skilled in the art of heat exchanger design and maintenance.

Depending on the concentration of diamondoid compounds in the natural gas stream as well as on the operating temperature and pressure, discontinuation of the solvent charge may precipitate partial or complete plugging of at least a portion of the process cooler heat exchange tubes. Such deposits may be removed via intermittent high dosage or "slug" solvent treatment. Slug solvent treatment has been found to be effective for removing diamondoid deposits from process cooler heat exchange tubes, e.g., charging 50 to 100 gallon slugs of solvent intermittently into the 10 to 15 MMSCF/D natural gas stream at a point upstream of the process cooler. The slugged solvent is then recovered by a method similar to that used for the continuously injected solvent, which method is described below.

The cooled mixture of natural gas and solvent 22 flows to production separator 30 where it is flashed to form an overhead vapor stream 32 and a bottom liquid stream 34. Production separator 30 is illustrated as a flash drum, i.e. a single stage vapor-liquid separation device, but may also comprise any suitable vapor-liquid separation apparatus known to those skilled in the art of process equipment design.

A first portion of the overhead vapor stream 32 flows through control valve 36 to enter sorption zone 40 while a second portion of the overhead vapor stream flow is preferably diverted by control valve 36 to form regeneration gas stream 38. The total overhead vapor stream may be charged to the sorption zone if an inert gas stream for use as a regeneration gas is both inexpensive and easily piped into the sorption process equipment. It is generally preferred, however, to use a portion of the overhead vapor stream as a regeneration gas due to its inherent economy and availability. Regeneration gas flow to the silica gel sorption zone is preferably countercurrent, i.e., gas flow for silica gel desorption during regeneration should be oriented in the opposite direction from gas flow for silica gel sorption during gas purification operation.

The first portion of the overhead vapor stream 32 then contacts a silica gel sorbent contained in sorption zone 40. The overhead vapor stream preferably flows downwardly in contact with the silica gel sorbent through the length of the sorption zone 40. Silica gel volume is preferably selected such that almost all of the silica gel sorption capacity is utilized before regeneration.

The purified gas stream 42 is then withdrawn from sorption zone 40 and charged to pipeline or storage facilities. The second portion of the overhead vapor stream is preferably diverted for use as a regeneration gas as described above. Regeneration gas 38 is heated in regeneration heat exchanger 50 to a temperature less than 315° C. (600° F.), preferably between about 177° and 288° C. (350° and 550° F.) and then charged to the bottom of sorption zone 60 to countercurrently desorb water and heavy hydrocarbons, particularly diamondoids, from the silica gel. The length of the regeneration step is a function of regeneration gas temperature and flowrate as well as the amount of sorbed material contained in the silica gel sorption bed. These operating parameters may be varied to synchronize the regeneration cycle (desorption) of a first sorption zone with the gas purification cycle (sorption) of a second sorption zone. The sorption zones are preferably piped and valved in a parallel configuration such that one sorption zone may be operated in the gas purification mode while the other sorption zone is countercurrently regenerated.

Enriched regenerated gas 62 is cooled to a temperature of between about 24 and 60° C. (75° and 140° F.) in regeneration cooler 70 and is flashed in regeneration separator 80 to form a overhead gas stream 82 and a liquid bottom stream 84. The overhead gas stream is preferably recycled and mixed with the production separator overhead stream and purified in sorption zone 40. The regeneration separator overhead gas stream 82 may optionally be mixed with purified gas stream 42. While such optional configuration beneficially reduces the total gas flow through the sorption zone operating in the gas purification mode, it necessarily reduces both diamondoid compound recovery and natural gas product purity.

Liquid bottom stream 34 from production separator 30 and 84 from regeneration separator 80 normally flow to solvent accumulator drum 90. A portion of the diamondoid-containing solvent 91 is drawn off the solvent accumulator and fresh solvent 94 is added downstream to maintain diamondoid concentration in the solvent below saturation. A water stream 93 is drawn off from solvent accumulator drum 90 and is sent to the process sewer for treatment and hydrocarbon recovery. The remaining diamondoid-containing solvent 92 is withdrawn from solvent accumulator drum 90, charged through pump 100 and mixed with fresh solvent 94 to form recycled solvent stream 18 which is added to the natural gas stream 16 upstream from process cooler 20 as described above.

A slip stream of diamondoid-containing solvent 96 may optionally be diverted from recycled solvent stream 18 and mixed with the enriched regeneration gas stream 62 upstream of regeration cooler 70. This slip steam addition to the enriched regeneration gas stream may be necessary to avoid diamondoid deposition in the regeneration gas cooler.

If the diamondoids contained in the feedstream to the present process consist predominately of adamantane and diamantane, it has been found that the two compounds may be effectively segregated and recovered separately. Given a feedstream in which the diamondoids principally consist of adamantane and diamantane, the liquid bottom streams from the production separator 30 and regeneration separator 80 have been found to be rich in diamantane and adamantane, respectively. Thus to recover the two compounds at relatively high purity, streams 35 and 85 are drawn off of streams 34 and 84, respectively, and are routed to separate diamondoid recovery processes (not shown).

EXAMPLES

Well No. 1

The production cooler (air cooled fin-fan heat exchanger) of Well No. 1 was taken out of service due to unacceptably high pressure drop across the exchanger. The heat exchange tubes, particularly the first several passes, were found to be plugged with a crystalline deposit which was analyzed and determined to be a mixture of diamondoid compounds rich in adamantane and diamantane.

Day 1 — The tubes were flushed with diesel fuel until mechanically clean and returned to service.

Day 2 — Intermittent injection of 50—100 gallon slugs of diesel fuel containing a minor amount of KW-151 and KP-111 brand corrosion inhibitors distributed by the Petrolite Company of St. Louis, MO was initiated upstream of the production cooler. The average slug injection rate ranged between 1 and 2 slugs per day. The natural gas flowrate from Well No. 1 remained between 10 and 15 MMSCF/D .

Day 173 — Slug injection was discontinued and continuous injection of diesel fuel at 2–4 GPM was initiated.

Day 316 — No variation in process conditions indicative of accumulating diamondoid solids. Visual inspections of process internals revealed no further accumulation of diamondoid solids. Analysis of circulating diesel fuel shows progressive increase in diamondoid content further indicating successful ongoing diamondoid extraction.

Well No. 2

Day 2 — Intermittent injection of 50—100 gallon slugs of diesel fuel containing a minor amount of KW-151 and KP-111 brand corrosion inhibitors was initiated upstream of the production cooler in Well No. 2. The average slug injection rate ranged between 1 and 2 slugs per day. The natural gas flowrate for Well No. 2 remained between 10 and 15 MMSCF/D.

Day 110 — Slug injection was discontinued and continuous injection of diesel fuel at 2–4 GPM was initiated.

Day 168 — No variation in process conditions indicative of accumulating diamondoid solids. Visual inspections of process internals revealed no further accumulation of diamondoid solids. Analysis of circulating diesel fuel shows progressive increase in diamondoid content further indicating successful ongoing diamondoid extraction.

Well No. 3

Day 2 — Intermittent injection of 50–100 gallon slugs of diesel fuel containing a minor amount of KW-151 and KP-111 brand corrosion inhibitors was initiated upstream of the production cooler in Well No. 3. The average slug injection rate ranged between 1 and 2 slugs per day. The natural gas flowrate for Well No. 3 remained between 10 and 15 MMSCF/D.

Day 173 — Slug injection was discontinued and continuous injection of diesel fuel at 2–4 GPM was initiated.

Day 316 — No variation in process conditions indicative of accumulating diamondoid solids. Visual inspections of process internals revealed no further accumulation of diamondoid solids. Analysis of circulating diesel fuel shows progressive increase in diamondoid content further indicating successful ongoing diamondoid extraction.

Changes and modifications in the specifically described embodiments can be carried out without departing from the scope of the invention which is intended to be limited only by the scope of the appended claims.

We claim:

1. A process for extracting diamondoid compounds from a gas stream comprising the steps of:

(a) providing a gas stream containing a recoverable concentration of diamondoid compounds;

(b) mixing said gas stream containing diamondoid compounds with a solvent in which diamondoid compounds are at least partially soluble;

(c) controlling the conditions including temperature and pressure of said mixture of step (b) above to maintain at least a portion of said mixture in the liquid phase;

(d) separating said mixture under the controlled conditions of step (c), above into a vapor stream and a diamondoid-enriched solvent stream; and (e) recovering diamondoid compounds from said diamondoid-enriched solvent stream.

2. The process of claim 1 further comprising recycling said diamondoid-enriched solvent stream of step (d) to at least partially saturate said diamondoid-enriched solvent stream.

3. The process of claim 2 further comprising adding fresh solvent and withdrawing solvent which is at least partially saturated with diamondoid compounds.

4. A process for extracting diamondoid compounds from a natural gas stream comprising the steps of:

(a) providing a natural gas well containing a recoverable concentration of diamondoid compounds;

(b) withdrawing natural gas containing diamondoid compounds from said natural gas well of step (a), above;

(c) mixing said withdrawn natural gas with a solvent in which diamondoid compounds are at least partially soluble;

(d) controlling the conditions including temperature and pressure of said mixture of step (c) above to maintain at least a portion of said mixture in the liquid phase;

(e) separating said mixture under the controlled conditions of step (d), above into a vapor stream and a diamondoid-enriched solvent stream; and (f) recovering diamondoid compounds from said diamondoid-enriched solvent stream.

5. The process of claim 4 wherein step (d) further comprises cooling said mixture of step (c).

6. The process of claim 5 wherein said cooling step comprises reducing the temperature of said mixture of step (c) to a temperature between about 24° and 60° C. (75° and 140° F.).

7. The process of claim 4 further comprising recycling said diamondoid-enriched solvent of step (e) to at least partially saturate said solvent with diamondoid compounds.

8. The process of claim 7 further comprising adding fresh solvent and withdrawing at least partially saturated diamondoid-enriched solvent to maintain the circulating solvent inventory at a diamondoid concentration below solvent saturation.

9. The process of claim 5 further comprising depressuring said natural gas stream to a pressure of not more than 21,000 kPa (3000 psig).

10. A process for extracting diamondoid compounds from a diamondoid-containing gas stream comprising the steps of:

(a) providing a gas stream containing a recoverable concentration of diamondoid compounds;

(b) contacting said diamondoid-containing gas stream with silica gel in a sorption zone for a period of time sufficient for said silica gel to sorb at least a portion of said diamondoid compounds from said hydrocarbon gas; and (c) regenerating said silica gel by contacting said silica gel with a regeneration fluid in which diamondoid compounds are at least partially soluble to desorb diamondoid compounds from said silica gel.

11. The process of claim 10 wherein said silica gel contacting step (b) is carried out under conditions of temperature and pressure to prevent substantial formation of solid diamondoid desposits in said sorption zone 12. A process for extracting diamondoid compounds from a diamondoid-containing gas stream comprising the steps of:

(a) providing a gas stream containing a recoverable concentration of diamondoid compounds;

(b) mixing said gas stream containing diamondoid compounds with a solvent in which diamondoid compounds are at least partially soluble;

(c) controlling the conditions including temperature and pressure of said mixture of step (b) above to maintain at least a portion of said mixture in the liquid phase;

(d) separating said mixture under the controlled conditions of step (c), above into a partially purified gas stream and a diamondoid-enriched solvent stream;

(e) recovering diamondoid compounds from said diamondoid-enriched solvent stream;

(f) contacting said partially purified gas stream with silica gel in a first sorption zone for a period of time sufficient for said silica gel to sorb at least a portion of said diamondoid compounds from said hydrocarbon gas; and (g) recovering diamondoid compounds from silica gel in a second sorption zone by contacting said silica gel with a regeneration fluid in which diamondoid compounds are at least partially soluble to desorb diamondoid compounds from said silica gel.

13. The process of claim 12 wherein said silica gel contacting step (f) is carried out under conditions of temperature and pressure to prevent substantial formation of solid diamondoid desposits in said sorption zone.

14. A process for separating adamantane from diamantane comprising the steps of:

(a) providing a gas stream containing a recoverable concentration of adamantane and diamantane;

(b) mixing said gas stream containing adamantane and diamantane with a solvent which solvates diamantane preferentially to adamantane, (c) controlling the conditions including temperature and pressure of said mixture of step (b) above to maintain at least a portion of said mixture in the liquid phase;

(d) separating said mixture under the controlled conditions of step (c), above into a adamantane-enriched gas stream and a diamantane-enriched solvent stream;

(e) recovering diamantane from said diamantane-enriched solvent stream;

(f) contacting said adamantane-enriched gas stream with silica gel in a first sorption zone for a period of time sufficient for said silica gel to sorb at least a portion of adamantane from said adamantane-enriched gas; and (g) recovering adamantane from silica gel in a second sorption zone by contacting said silica gel with a regeneration fluid in which adamantane is at least partially soluble to desorb adamantane from said silica gel.

15. The process of claim 14 wherein said silica gel contacting step (f) is carried out under conditions of temperature and pressure to prevent substantial formation of solid diamondoid desposits in said sorption zone.

16. The process of claim 1 wherein said solvent is a petroleum hydrocarbon.

17. The process of claim 16 wherein said solvent is diesel fuel.

18. The process of claim 4 wherein said solvent is a petroleum hydrocarbon.

19. The process of claim 18 wherein said solvent is diesel fuel.

20. The process of claim 10 wherein said solvent is a petroleum hydrocarbon.

21. The process of claim 20 wherein said solvent is diesel fuel.

22. The process of claim 14 wherein said solvent is a petroleum hydrocarbon.

23. The process of claim 22 wherein said solvent is diesel fuel.

* * * * *

UNITED STATES PATENT AND TRADEMARK OFFICE
CERTIFICATE OF CORRECTION

PATENT NO. : 4,952,748

DATED : 8/28/90

INVENTOR(S) : R.A. Alexander et al

It is certified that error appears in the above-identified patent and that said Letters Patent is hereby corrected as shown below:

Col. 1, line 3, insert after title --The present application is related by the disclosure of similar subject matter to commonly-assigned Applications Serial Nos. 358,760; 358,759; and 358,761, filed concurrently herewith.--

Signed and Sealed this

Twenty-fifth Day of February, 1992

*Attest:*

HARRY F. MANBECK, JR.

*Attesting Officer*

*Commissioner of Patents and Trademarks*